United States Patent [19]

Aroonsakul

[11] Patent Number: 4,727,041
[45] Date of Patent: Feb. 23, 1988

[54] METHOD OF DIAGNOSING ALZHEIMER'S DISEASE

[76] Inventor: Chaovanee Aroonsakul, 151 N. Michigan Ave., Suite 1916, Chicago, Ill. 60601

[21] Appl. No.: 852,645

[22] Filed: Apr. 16, 1986

[51] Int. Cl.[4] ..................... G01N 31/00; G01N 33/00
[52] U.S. Cl. ........................................ 436/8; 424/9; 436/811; 436/500; 436/87
[58] Field of Search ................ 424/288, 9; 436/8–18, 436/500, 504, 542, 544, 87, 89, 811

[56] References Cited

PUBLICATIONS

Newsletter, Alzheimer's Disease and Related Disorders Association, Jun., Jul., 1984, pp. 1–2, 10.
Hormones, Facts and Comparisons, Jan. 1983, pp. 95–114.
The Andrenocortical Hormones, Endocrinology and Reproduction, pp. 1019 & 1032.
Product Information, Physicians Desk Reference, 38 edition, 1984, pp. 695, 911–912.
The Pharmacological Basis of Therapeutics, pp. 315, 319, 322–323, 1538–1540, 1566–1569.
Dementia, Textbook of Medicine, pp. 102–103.
Paralysis Agitans, Current Diagnosis & Treatment, 1968, pp. 560–562.
The Nervous System, Diseases of the Nervous System, p. 752.
Aged Limbic System, Interactions of Estrogen with Catecholaminergic and Peptidergic Synaptic Transmission, Biomedical Research, 1981, pp. 85–108.
Reformation in Adult Rats of Functional Septo-Hippocampal Connections by Septal, et al, Neuroscience Letters, 1981, pp. 7–12.
Modification of Synapses in Androgen-Sensitive Muscle, The Journal of Neuroscience, Mar. 1984, pp. 786–792.
Alzheimer's Disease, pp. 62–74.
Estradiol Increases Choline Acetyltransferase Activity in Specific Basal Forebrain Nuclei and Projection Areas of Female Rats, Exp. Neurology, 484–490.
Research on Aging Burgeons as More Americans Grow Older, Medical News, Mar. 8, 1985, pp. 1369–1376, 1385, 1405.
Alzheimer's Victims Respond Well to Injections of Drug, Chicago Tribune, Oct. 21, 1984, p. 3.
Glossary, United Parkinson Foundation, May, 1982, Parkinson's Disease: Biochemical and Etiologic Considerations, Neurologic Consultant, pp. 1–8.
Transplanting Cells Into Brain Offers Promise as a Therapy, pp. 17, 20.
Degenerative Diseases of the Nervous System, Harrison's Principles of Internal Medicine, pp. 1919–1921.
Care of the Dementia Patient, pp. 4–8.

*Primary Examiner*—Deborah L. Kyle
*Assistant Examiner*—T. J. Wallen

[57] ABSTRACT

A method of diagnosing Alzheimer's disease by the determination of the levels of the hormones somatotropin (human growth hormone) and somatomedin-C (IGF-I) after the administration of the L-dopa provocative test. Blood-sera samples are taken every thirty minutes for a two hour period after the administration of L-dopa, and the samples are tested for the levels of these hormones. These levels are then compared against the levels for normal subjects in the age group of between fifty and sixty. If the levels of the patient being diagnosed falls below the statistical mean corrected for error, then a diagnosis of Alzheimer's disease is indicated.

21 Claims, 2 Drawing Figures

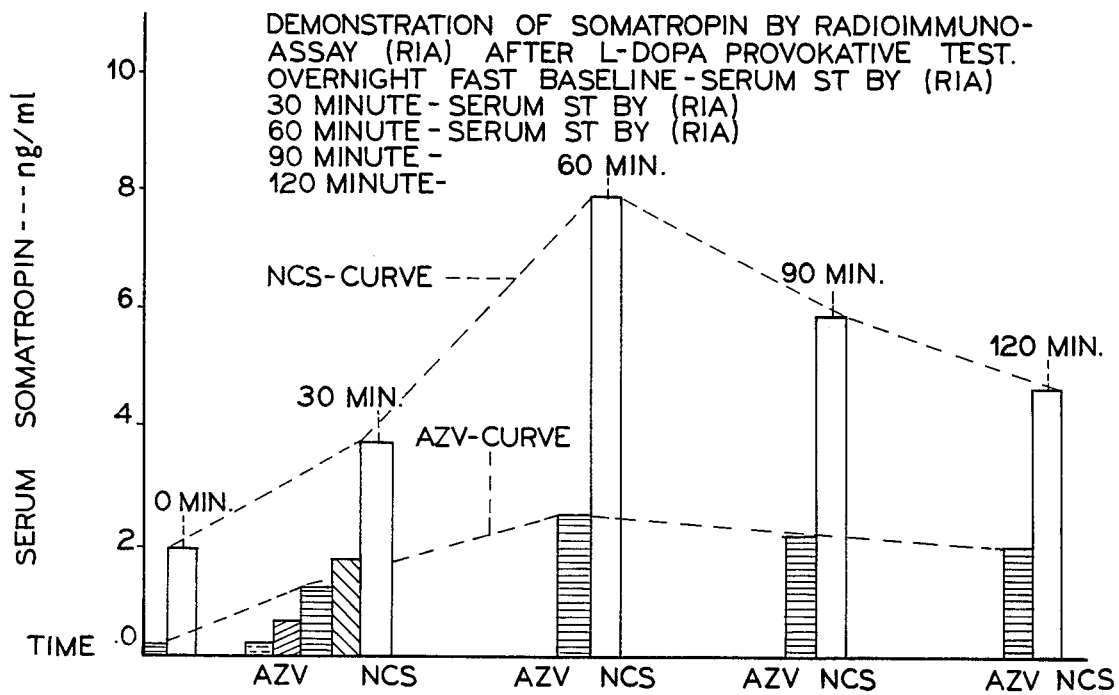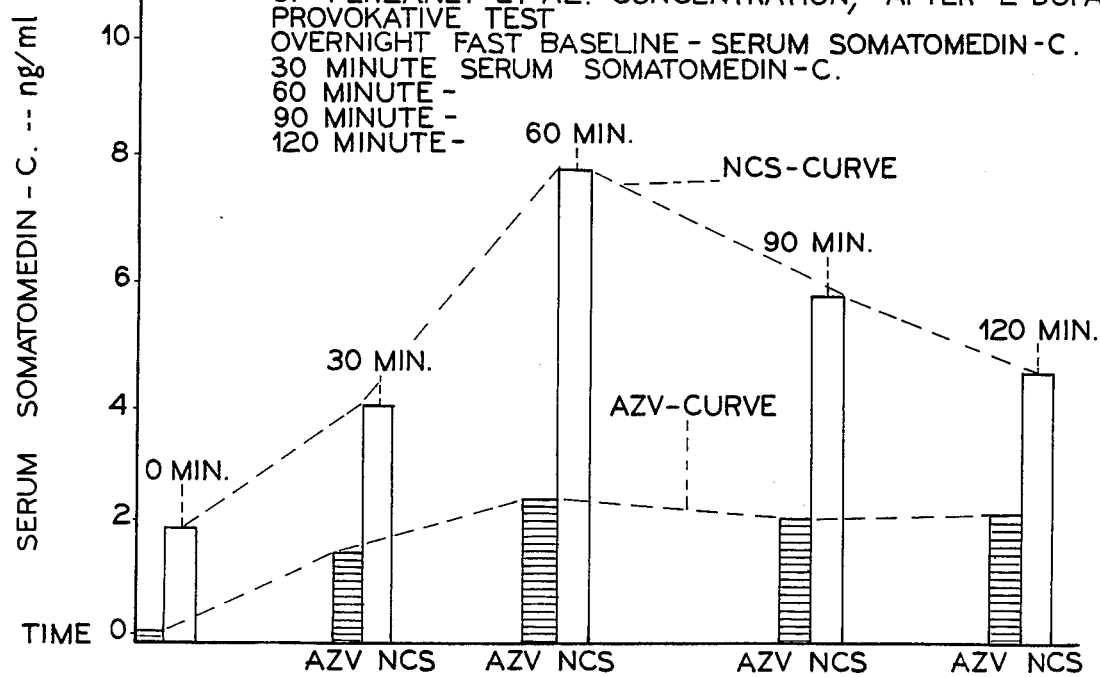

METHOD OF DIAGNOSING ALZHEIMER'S DISEASE

BACKGROUND OF THE INVENTION

The present invention is directed to a method of diagnosing Alzheimer's Disease in human beings. Alzheimer's disease is the fourth leading cause of death in the United States, the precise cause of which is not yet known. At present, it is a difficult and time-consuming task to definitively determine whether a patient is suffering from Alzheimer's disease or another ailment having similar manifestations and/or symptoms. Presently-used techniques for determining Alzeimer's Disease include neuropsychological testing which compares the mental status of the patient relative to a norm, as well as the patient's cognitive dysfunction. Such testing also tests for mood depressions, agitation, irritability, and the like, all of which are symptoms of Alzheimer's disease when combined with other diagnostic indications. These other diagnostic tools and methods are: The use of a brain atlas beam test or EEG (electroencephalogram) which demonstrate increases in delta and theta waves. Further, CAT scans of the brain or nuclear magnetic resonance (NMR) are used in the diagnosis by showing reduced uptakes of the brain's cells in the temporal areas or at the hippocampal region, which is a sign of cortical atrophy, associated with Alzheimer's disease, since the cortex and hippocampus of the brain are those usually affected by Alzheimer's disease, such effect being caused, it is believed, by the deficiency of the enzyme choline acetyltransferase (CAT). Choline acetyltransferase is the chemical messenger from the nucleus basalis to the cortex. Still another method used in the diagnosis of Alzheimer's disease, based upon the fact that it has been discovered that in Alzheimer's patients the brain is found to have consumed from 30%–50% less glucose in each of the four cortical regions and one subcortical region is the PET scan. The reduction of consumption of glucose in these portions of the brain is, it is generally believed, to result from the deficiency of the enzyme phosphofructokinase, which is necessary for the conversion of glucose to high-energy intermediates. The determination of glucose reduction in these portions of the brain is typically carried out by the PET scan, which detects the presence of the glucose analogue (F-18)-2-fluoro-2-deoxy-D-glucose (FDG).

It has hitherto been the conventional practice of determing a diagnosis of Alzheimer's disease by the positive indication by any of the above-mentioned tests. However, the results of these tests are often not definitive, since any one or more of them may show that the symptoms are not those of Alzheimer's disease even though the patient may be suffering therefrom. On the other hand, each of the above-mentioned tests may show that the diagnosis is that of Alzheimer's disease, when, in fact, it is not. The frequency of these false positives may be high. For example, a false positive may occur if the patient is suffering from neurosyphylis, follic acid deficiency, Vitamin B12 deficiency, hypothyroidism, encephalitis, electrolyte imbalance, drug toxicity, other metabolic disorders, virus infection of CNS, as well as others.

It is, of course, most important that a correct diagnosis be determined in order to decide upon the best treatment. The present invention is directed to a novel diagnosis for Alzheimer's disease that may be used in conjunction with other standard testing methods, or may be used alone for such determination, since it has been found to be very accurate, especially in conjunction with the fact that the other known diseases by which similar indications may result, as to those of the method of the present invention, are not at all likely to affect the patient for whom Alzheimer's disease may be a likely diagnosis.

It has been known that the drug levadopa (L-dopa), a common drug for treating Parkinson's disease, causes increased secretion of the growth hormone somatotropin (HGH-human growth hormone). This finding of L-dopa's provocative stimulation of the pituitary gland to secrete HGH was used as the basis for viewing the functioning of the peripheral nervous system (PNS) as an aminergic neuronetwork. Furthermore, since the hormone somatomedin-C (often referred to as IGF-I, for insulin-like growth factor, since it resembles insulin in many ways) is directly dependent upon the secretion of HGH by the pituitary gland, there has been established a direct linkage between increased secretion of HGH and increased production of the hormone somatomedin-C, which is produced chiefly in the liver and kidneys. The use of L-dopa to markedly increase the secretions of somatotropin and, consequently, the production of somatomedin-C in the human body has led to what is generally termed the "L-dopa provocative test." This test is used to determine the normal functioning of the anterior region of the pituitary gland responsible for the HGH production. Generally, the L-dopa provocative test is used by detecting the increases of HGH and IGF-I in a blood serum by the use of radioimmunoassay (RIA), which determines the presence or absence or the amounts of a certain hormone in a serum by the use of a radioactive agent, used in vitro. Radioimmunoassay techniques were first discovered by the observation that unlabelled insulin displaces radioactive iodine-labelled insulin from insulin antibodies, in vitro. With the antibody concentration and radiodinated antigen held constant, the binding of the label is quantitatively related to the amount of unlabelled antigen that is added. Thus, any amount of an unlabelled antigen may be determined by the known standards therefor. The amount of unlabelled antigen in a serum-sample can be guaged by measuring the fraction of bound, labelled antigen in its presence from a standard. RIA involves separation of the labelled antigen that is of interest into bound-unbound fractions after the interaction with an antibody in the presence of the unknown quantity of unlabelled antigen to be measured. RIA has been used in the past for the measuring of the amount of HGH in a serum taken from a subgroup of children, for treating diseases in children related to growth. The radioactive element used in this determination is usually I-125.

Somatotropin is a growth hormone (polypeptide link amino acid in character) secreted by the anterior region of the pituitary gland, which is most known for its capability of causing growth of the human skeleton. This is also known as the human growth hormone (HGH), and is the precursor of the hormone somatomedin-C (IGF-I), produced by the liver and kidneys. According to the present invention, it has been discovered that patients suffering from Alzheimer's disease have a deficiency of somatotropin production which leads to a deficiency of somatomedin-C levels, and that exogenous stimulation by a drug to cause increased secretions of HGH in normal human subjects does not function normally in Alzheimer's patients. Though it has been known to have increased levels of IGF-I in the blood with reduced levels of HGH, these instances are rare and can be taken into consideration when determining the diagnosis according to the present invention.

In applicant's copending application Ser. No. 666,254, filed on Oct. 29, 1984, it is disclosed that a method of treating Alzheimer's disease is by the administration of somatotropin, plus other anabolic hormones (Sex anabolic hormone, somatomamotropin, placental lactogen, trophoblastic hormonal factor).

SUMMARY OF THE INVENTION

It is, therefore, the primary objective of the present invention to provide a novel diagnostic technique and method by which positive identification of Alzheimer's disease in a human being may be established definitively.

It is another objective of the present invention to provide a novel diagnostic method to be used in conjunction with presently-available and presently-used techniques for the determination of Alzheimer's disease.

It is yet another objective of the present invention to provide another technique for diagnosing Alzheimer's disease in human beings that is easily performed by conventional radioimmunoassay techniques.

It is still another objective of the present invention to provide for the use of the diagnostic method of the present invention over a period of two days using the L-dopa provocative test, by which the levels in blood-sera of the hormones somatotropin and somatomedin-C are guaged and compared with levels in blood-sera of normal persons within the same age range, it having been discovered that a depletion and lack of efficacious capability of producing these two hormones in the body indicates a strong likelihood that the patient is suffering from Alzheimer's disease.

It is also an objective of the present invention to use any dopinamergic drug causing immediate excess secretion of the hormones HGH and IGF-I, as well as any drug creating the same excess secretion.

According to the novel method of diagnosing Alzheimer's dDisease of the present invention, the patient suspected of suffering from this disease is subjected to the L-dDopa provocative test, by which a specified dosage is administered on a first day, and followed on the next day with a higher dosage, immediately after which blood-serum samples are taken at 30 minute intervals, up to 120 minutes after the initial administration of the L-dopa on the second day, for subsequent analysis by RIA techniques in order to determine the absolute and relative levels of somatotropin and somatomedin-C hormones in each sample, for subsequent comparison with levels of normal persons in the same age bracket. By comparing the test-sample levels with those of normal persons, a firm diagnosis of Alzheimer's disease may be made, if the increases of these hormones fall below a critical value established by statistical techniques based on normal subjects.

BRIEF DESCRIPTION OF THE DRAWING

The invention will be more readily understood with reference to the accompanying drawing, wherein FIG. 1 is a bar-chart showing the levels of the hormone somatotropin in blood sera at the end of 30 minutes, 60 minutes, 90 minutes and 120 minutes, as well as at the time of initial administration, obtained from the results of the L-dopa provocative test, for determining levels thereof relative to a statistical average of normal subjects according to the method of the present invention for diagnosing Alzheimer's disease in human beings; and FIG. 2 is a bar-chart similar to FIG. 1 showing the same information for the hormone somatomedin-C.

DETAILED DESCRIPTION OF THE INVENTION

In order to properly diagnose Alzheimer's disease, it has been discovered that patients suffering from this disease suffer from a depletion of the human growth hormone somatotropin (HGH) and the HGH-dependent hormone somatomedin-C(IGF-I), which makes connective tissue die on skin and joints, the growth hormone being secreted by the pituitary gland, while somatomedin-C being secreted mainly by the liver and kidneys by stimulation of somatotropin. This discovery of the lack of proper levels of these two hormones, in combination with the fact that Alzheimer's disease patients lack the capabilities of producing these hormones endogenously even when exogenous stimuli are created in the body of the patient, has led to the method of diagnosis of the present invention. According to the present invention, the L-dopa provocative test is used to cause increased secretions of these two hormones, to determine if the pituitary gland, and the liver and kidneys, are capable of producing these hormones in response to this provocative test. It is important that not only the absolute levels of these two hormones in the peripheral blood serum be tested before the L-dopa provocative test, but also the levels of increase, if any, produced by the L-dopa provocative test, in order to determine the current stimulation-capabilities of the peripheral nervous system and the hyopthalamus, as well as the beta-andrenergic, alpha andrenergic, and dopaminergic control systems. It is believed that the dominant control system is the dopaminergic, which is why L-dopa causes increased secretions of HGH. For example, clonidine causes adrenergic stimulation of the brain which will increase HGH.

The secretion of somatotropin by the pituitary gland is dependant upon many factors, some of them being well-known, such as physical exercise, physical and hypoglycemic emotional stresses, low-protein intake, and others. Endogenous triggers of HGH release include sleep. Whether exogenous or endogenous, the changes in the secretion of the growth hormone somatotropin by the pituitary gland are directly dependant upon by the hormone "growth-hormone releasing-hormone" (GHRH) produced by the hypothalamus, which acts directly upon the pituitary gland to cause increased secretion of HGH. Exogenous injection of GHRH into the blood system will result in direct increased secretion of HGH. The secretion of HGH, in turn, causes the increased secretion of somatomedin-C by the liver and kidneys, which somatomedin-C is also used as a feedback loop to the hypothalamus to regulate the secretion of GHRH, and, thus, the secretion of HGH. The secretion of HGH is also inhibited by the hormone somatostatin, a cyclic peptide having fourteen amino acids, produced by the pancreas. Somatostatin also acts in a feedback loop with the hypothalamus to inhibit production of GHRH and HGH.

It has been the discovery according to the present invention that patients suffering from Alzheimer's disease lack proper and normal levels of HGH and somatomedin-C, and also lack the capabilities of producing increased amounts of these hormones in response to exogenous stimuli that tend to cause substantially immediate and large increases of secretions in these two hormones, such as occurs during the L-dopa provocative test. It is the method of the present invention to use the L-dopa provocative test to cause sudden and substantial increases in the secretions of the hormones HGH and somatomedin-C. By using radioimmunoassay techniques for detcting the levels of these hormones in the blood serum at chosen time intervals, the results thereof may be compared with the norm for the age of the patient, to thereby guage if the pituitary gland is capable of reacting to this stimuli to increase production of HGH, so that a firm diagnosis may be made of Alzheimer's disease.

According to the method of the present invention for diagnosing Alzheimer's disease, one day prior to the use of the L-dopa provocative test, a dosage of 8 mg. per kilogram-of-weight of the patient is administered to the patient to activate the HGH-secreting capabilities of the pituitary gland. On the next day, after an overnight fast, the L-dopa provocative test is given, with a dosage of 15 mg. per kilogram-of-weight of the patient. A blood sample is taken just prior to the dosage of 8 mg./kg. on the day prior to the L-dopa provocative test, and blood samples are also taken immediately before the start of the L-dopa provocative testing, and every thirty minutes after the dosage of 15 mg./kg. has been administered. Each blood serum is then tested by RIA techniques to determine the absolute levels of somatotropin and somatomedin-C, and compared against the normal values for the age of the patient being tested. Referring to FIG. 1, there is shown a bar-chart comparing the levels of somatotropin and somatomedin-C obtained by RIA techniques for the five blood sera taken during the L-dopa provocative test with the levels for normal subjects aged fifty and over. The shaded bars represent typical levels of a patient resulting from Alzheimer's disease, while the unshaded bars indicate the levels for a normal person aged fifty and over, for the five sera assayed. As can be seen, for normal subjects, the readings at times: Zero minutes, thirty minutes, sixty minutes, ninety minutes, and one-hundred-twenty minutes are, approximately: 2.00 ng/ml; 3.75 ng/ml; 7.90 ng/ml; 6.05 ng/ml; and 4.45 ng/ml. For patients suffering from Alzheimer's disease, the corresponding values are, approximately: 0.02 ng/ml; between 0.03 ng/ml and 1.85 ng/ml; 2.15 ng/ml; 2.05 ng/ml; and 1.85 ng/ml. The values indicated for the normal subjects are the statistical mean average. The highest value shown in FIG. 1 for a patient suffering from Alzheimer's disease for each of the sera tested by RIA is that lying outside of the standard statistical error associated with the RIA testing.

FIG. 2 shows similar results for the RIA of the hormone somatomedin-C. For normal subjects age fifty and over, the values from RIA of this hormone are, approximately: 1.95 ng/ml; 4.00 ng/ml; 8.05 ng/ml; 5.90 ng/ml; and 4.45 mg/ml. The corresponding values of Alzheimer's disease patients, are, approximately: 0.10 ng/ml; 1.65 ng/ml; 2.15 ng/ml; 2.00 ng/ml; and 2.05 ng/ml.

It is, of course, possible to use different time periods in which the blood sera are taken for subsequent RIA analysis, with these results being compared to a standard for subjects aged fifty and over for the same time periods tested. According to the present invention, substantial differences in levels of these two hormones during the L-dopa provocative test as compared with the normal subjects is a positive and definitive indication of Alzheimer's disease. Furthermore, the absolute differences between the tested sera and the levels for normal subjects may also be used for an indication as to stage of advancement of Alzheimer's disease in the patient. Tested levels far outside the statistical norm adjusted for standard statistical error would mean a more advanced stage of the disease.

There will be some instances where the levels of somatotropin will increase and be similar to those of normal subjects, but the levels of somatomedin-C will fall far short than those for normal subjects, as could occur if the patient were suffering from liver disease. Thus, the L-dopa provocative test would show a mixed result. In this case, further testing would be required, and a positive determination of Alzheimer's disease would have to be confirmed in conjunction with other, currently-used, prior-art methods of diagnosis, such as EEG testing, neuropsychological testing, and the like. Also, where the results from the L-dopa provocative test do not show enough differences between the patient being tested and the norm, such as might occur if the values determined by RIA were not outside the statistical mean error of the normal group, then these other conventional methods of diagnosis would be used in conjunction with the method of the present invention. Whereas, both HGH and IGF-I deficiency in children may occur, as in dwarfism, in adults such matched deficiency is not known to indicate any other disease other than discovered according to the present invention. Since during basal, morning conditions there usually cannot be detected any differences between normal subjects and those with HGH deficiency, the provocative test is required, as described above.

Any other HGH-provocative agent may be used instead of L-dopa. For example, bromocriptine, propanolol, clonidine, other dopaminergic stimuli, and glucagon, a small peptide that mediates the flow of glucose to insulin-independent tissues. Of course, the time periods between which the blood sera are taken will depend upon the somatotropin-provocative agent used. Other constraints and conditions will, of course, change dependent upon the HGH-provocative used, and will be obvious to one having ordinary skill in the art. For example, for glucagon as the HGH-provocative, overnight fasting would not be required.

While a specific embodiment of the invention has been set forth, it is to be understood that numerous changes, modifications, and alterations to the present method for diagnosing Alzheimer's disease may be made without departing from the scope and spirit of the invention as set forth in the appended claims.

What is claimed:

1. A method of diagnosing Alzheimer's disease in human beings comprising the steps of;
 (a) subjecting a patient suspected of suffering from Alzheimer's disease to a somatotropin secretion-stimulation test;
 (b) determining the levels of somatotropin in at least one blood serum sample taken from the patient after the somatotropin secretion-stimulation test; and
 (c) comparing the levels of somatotropin from the at least one blood serum sample, obtained during said step (b) with the levels of somatotropin found in normal subjects within the patient's age group to determine if any increases of somatotropin caused by said step (a) statistically-match the increases thereof found in normal subjects.

2. The method of diagnosing Alzheimer's disease according to claim 1, further comprising the steps of:
   (d) determining the levels of the hormone Somatomedin-C in the at least one blood serum sample after said step (a); and
   (e) comparing the levels of Somatomedin-C found from said step (d) with the levels of Somatomedin-C found in normal subjects within the patient's age group to determine if any increases of somatomedin-C caused by said step (a) statistically-match the increases thereof in the normal subjects.

3. The method of diagnosing Alzheimer's disease according to claim 2, wherein said step (a) comprises administering a L-dopa provocative test to the patient suspected of suffering from Alzheimer's disease.

4. The method of diagnosing Alzheimer's disease according to claim 2, further comprising the step of testing the patient suspected of suffering from Alzheimer's disease by at least one other conventional test for diagnosing Alzheimer's disease in a patient, in order to confirm and corroborate the findings from said steps (a) through (e).

5. The method of diagnosing Alzheimer's disease according to claim 2, wherein each of said steps (c) and (e) comprises comparing the levels obtained from said steps (b) and (d), respectively, with the statistical mean minus the statistical error for normal persons aged between 50 and 60, so that, if the levels from said steps (b) and (d) fall outside thereof, a diagnosis of Alzheimer's disease is indicated.

6. The method of diagnosing Alzheimer's disease according to claim 5, wherein said step (a) comprises administering the L-dopa provocative test to the patient suspected of suffering from Alzheimer's disease.

7. The method of diagnosing Alzheimer's disease of claim 2 wherein step (a) includes administering to the patient at least one agent chosen from the group consisting of: L-dopa, bromocriptine, propanolol, glucagon, and clondine in sufficient dosages so as to tend to cause a sudden dramatic increase in the secretions of somatomedin-C.

8. The method of diagnosing Alzheimer's disease of claim 2 wherein step (a) includes administering to the patient at least one agent chosen from the group consisting of: L-dopa, bromocriptine, propanolol, glucagon, and clondine in sufficient dosages so as to tend to cause sudden dramatic increase secretions of somatomedin-C and somatotropin.

9. The method of diagnosing Alzheimer's disease according to claim 1, wherein said step (a) comprises administering a L-dopa provocative test to the patient suspected of suffering from Alzheimer's disease.

10. The method of diagnosing Alzheimer's disease according to claim 9, wherein said step (a) comprises: taking sample-sera from the patient being tested every thirty minutes after administration of L-dopa of the L-dopa provocative test.

11. The method of diagnosing Alzheimer's disease according to claim 10, wherein five sample-sera are taken for analysis during said step (b).

12. The method according to claim 11, wherein one of said sample-sera is taken immediately prior to the administration of the L-dopa of said step (a), and the remainder of said sample-sera being taken every thiry minutes thereafter until one-hundred-twenty minutes after administration of the L-dopa.

13. The method of diagnosing Alzheimer's disease according to claim 9, wherein said step (a) comprises administering approximately 15 mg/kg-of-weight of the patient being tested.

14. The method of diagnosing Alzheimer's disease according to claim 13, further comprising administering a dosage of L-dopa on the day before said step (a) is performed.

15. The method of diagnosing Alzheimer's disease according to claim 14, wherein said dosage of L-dopa on the day before said step (a) is approximately 8 mg/kg-of-weight of the patient.

16. The method of diagnosing Alzheimer's disease according to claim 1, wherein step (a) includes administering to the patient being diagnosed at least one agent chosen from the group consisting of L-dopa, bromocriptine, propanolol, glucagon, and clonidine in sufficient dosages so as to tend to cause sudden, dramatic, increased secretions of somatotropin.

17. The method of diagnosing Alzheimer's disease according to claim 1, wherein said step (c) comprises comparing the levels obtained from said step (b) with the statistical means minus the statistical error for normal persons aged between 50 and 60, so that, if the levels from said step (b) fall outside thereof, a diagnosis of Alzheimer's disease is indicated.

18. A method of diagnosing Alzheimer's disease, in which the L-dopa provocative test, or the equivalent thereof, has been given the patient being diagnosed, comprising:
   (a) determining the levels of at least one of the hormones somatotropin and somatomedin-C after the administration of the L-dopa, or the equivalent thereof; and
   (b) comparing the levels of at least one of somatotropin and somatomedin-C obtained from step (a) with levels of normal subjects within the same age bracket as the patient being tested for Alzheimer's disease, in order to determine if any increase, or lack thereof, in the levels from said step (a) falls below the statistical levels of the normal subjects.

19. The method of diagnosing Alzheimer's disease according to claim 18, wherein said step (a) comprises determining the levels of both said hormones from blood samples taken every thirty minutes after the administration of the L-dopa, or the equivalent thereof, the last sample being taken at one-hundred-twenty minutes after the administration of the L-dopa, or the equivalent thereof.

20. The method of diagnosing Alzheimer's disease according to claim 19, wherein said step (a) further comprises taking blood samples immediately preceding the administration of the L-dopa, or its equivalent, and one day before the administration thereof, and determining the levels of said hormones in each of said blood samples.

21. A method of diagnosing Alzheimer's disease comprising the steps of:
   (a) stimulating the secretion of somatotropin and somatomedin-C in a patient suspected of suffering from Alzheimer's disease;
   (b) determining the levels of somatotropin and somatomedin-C in at least one blood serum sample taken from the patient after step (a) has been performed; and
   (c) comparing the levels of somatotropin and somatomedin-C determined in step (b) to typical levels of somatotropin and somatomedin-C found in subjects who do not suffer from Alzheimer's disease of like age to the patient.

* * * * *